(12) United States Patent
Mitsui et al.

(10) Patent No.: US 7,705,175 B2
(45) Date of Patent: Apr. 27, 2010

(54) METHOD FOR PRODUCING IMIDE ETHER COMPOUND

(75) Inventors: Hitoshi Mitsui, Nara (JP); Yuichiro Kinoshita, Chiba (JP); Kazuya Nakagawa, Chiba (JP)

(73) Assignee: Nippoh Chemicals Co., Ltd., Chuo-Ku, Tokyo (JP)

( * ) Notice: Subject to any disclaimer, the term of this patent is extended or adjusted under 35 U.S.C. 154(b) by 2 days.

(21) Appl. No.: 11/795,404

(22) PCT Filed: Jan. 18, 2006

(86) PCT No.: PCT/JP2006/300598

§ 371 (c)(1),
(2), (4) Date: May 7, 2008

(87) PCT Pub. No.: WO2006/077854

PCT Pub. Date: Jul. 27, 2006

(65) Prior Publication Data

US 2009/0005599 A1    Jan. 1, 2009

(30) Foreign Application Priority Data

Jan. 18, 2005    (JP)    ............................. 2005-010947

(51) Int. Cl.
*C07C 249/00*    (2006.01)

(52) U.S. Cl. ........................ 558/6; 558/7; 558/8; 558/9

(58) Field of Classification Search ...................... 558/6
See application file for complete search history.

(56) References Cited

U.S. PATENT DOCUMENTS

| | | | |
|---|---|---|---|
| 4,111,976 A | | 9/1978 | Balke et al. |
| 4,727,142 A | * | 2/1988 | Fuss et al. .................. 544/216 |
| 4,743,701 A | * | 5/1988 | Mathew ......................... 558/7 |
| 6,806,380 B2 | * | 10/2004 | Kolb et al. ..................... 558/6 |

FOREIGN PATENT DOCUMENTS

| | | |
|---|---|---|
| JP | 54-098712 A | 8/1979 |
| JP | 54-98712 A | 8/1979 |
| JP | 55-73647 A | 6/1980 |
| JP | 61-028663 B2 | 7/1986 |
| JP | 61-28663 A | 12/1986 |
| JP | 03-220134 A | 9/1991 |
| JP | 2000-191618 A | 7/2000 |
| JP | 2000-191618 A | 7/2002 |
| JP | 2003-192650 A | 7/2003 |
| JP | 2003-321325 A | 11/2003 |
| JP | 2004-099443 A | 4/2004 |
| JP | 2004-99443 A | 4/2004 |

OTHER PUBLICATIONS

International Preliminary Report on Patentability/Written Opinion (Forms PCT/IB/326, PCT/IB/373 and PCT/ISA/237) mailed Aug. 2, 2007 in corresponding PCT/JP2006/300598, IB of WIPO, Geneva, CH; and English translation thereof (Forms PCT/IB/338, PCT/IB/373 and PCT/ISA/237).
International Search Report and PCT/ISA/237 for PCT/JP2006/300598 dated Apr. 4, 2006.
Office Action issued Jul. 31, 2009, in corresponding Chinese Application No. 2006800026293; and English translation thereof.
Supplementary European Search Report issued Aug. 25, 2009 in corresponding EP Application No. 06711867.9-2103.

* cited by examiner

*Primary Examiner*—Brian J Davis
(74) *Attorney, Agent, or Firm*—Buchanan Ingersoll & Rooney PC

(57) ABSTRACT

Provided is a method for producing an imide ether compound in high yield. The method is characterized in that a nitrile compound, an alcohol, and a hydrogen halide are continuously introduced into a flow reaction device comprising a mixer and a flow reactor, to be subjected to a reaction. Because a reaction proceeds in a ratio of 1:1 by a flow reactor, selectivity is improved and generation of by-products is decreased, and thus an imide ether compound can be efficiently produced.

11 Claims, 4 Drawing Sheets

METHOD FOR PRODUCING IMIDE ETHER COMPOUND

TECHNICAL FIELD

The present invention relates to a method for producing an imide ether compound, and more specifically the present invention relates to a method for producing an imide ether compound of high yield in a short period of time, by using a flow reaction device having a mixer and a flow reactor.

BACKGROUND ART

An imide ether compound is a useful compound as a raw material of ortho-ester compound or the like, which is widely used in medical drug, agricultural chemical and industrial fields. By subjecting an alphatic nitrile or an aromatic nitrile, alcohol and hydrogen chloride, as raw materials, to a reaction, an imide ether hydrochloride, which is solid at normal temperature, can be formed.

Several methods for producing an imide ether compound are also known, for example, a method for generating an acetimide ether hydrochloride is disclosed (JP-B-61-28663), wherein the first step is carried out to react an alcohol in an amount of 0.3 to 0.6 mole and hydrogen chloride in an amount of 1.0 to 1.5 moles, relative to 1 mole of acetonitrile, and then by the addition of 0.4 to 0.8 mole of the alcohol into the resultant reaction liquid, the second step is carried out to continue an acetimide etherification reaction in the co-presence of a dispersing medium. Because an objective substance is deposited as crystal with progress of the acetimide etherification, and thickening of slurry-like reaction liquid makes it difficult to introduce theoretical amount of hydrogen chloride gas, the first step is carried out while suppressing deposition of the crystal by using 0.3 to 0.6 mole of the alcohol in advance, and then acetimide etherification reaction is completed by the further addition of the alcohol to the resultant reaction liquid in carrying out the second step. It should be noted that the dispersing medium is added to secure fluidity in the second step.

In addition, a method for generating an alkyl imide ether hydrochloride by the addition of a nitrile compound into an alcohol solution dissolved with hydrogen chloride is also disclosed (JP-A-2000-191618). The present invention was developed in view of a problem that the method for blowing hydrochloric gas into an alcohol solution of an aliphatic nitrile generates simultaneously the heat of dissolution of hydrogen chloride into a solvent and the heat of reaction, and heat generation amount is too much, and thus makes control of reaction temperature difficult. Namely, by dissolving hydrogen chloride into the alcohol in advance, heat of dissolution of hydrogen chloride during the reaction is suppressed, thereby reaction temperature is controlled and workability is improved.

In the meantime, in the production step of a compound, various reaction apparatuses are used. For example, in a method for producing an alkaline metal salt of glycine in which glycinonitrile and alkaline metal hydroxide are subjected to a reaction in the presence of water solvent, the reaction is carried out using a stirring tank flow reactor pressurized so that partial pressure of ammonia becomes at least equal to or higher than 0.2 MPa, and the reaction of the resultant reaction solution is completed in a liquid-sealing type tubular flow reactor (JP-A-2003-192650). By introduction ammonia into the stirring tank flow reactor while increasing a pressure so that partial pressure of ammonia becomes at least equal to or higher than 0.2 MPa, the reaction can be completed in a liquid sealing state, without vaporization of by-produced ammonia gas, and coloring of the reaction solution can be suppressed by setting arbitrarily ammonia concentration in a system.

In addition, a method for producing a concoction containing skin cosmetic ingredients, by the procedure step for inducing the concoction or the like, containing skin cosmetic ingredients, by an apparatus having a microstructure unit such as a micro-mixer or the like, is known (JP-A-2003-321325). It is an object of this invention to attain homogenization by using a micro-mixer or the like, in view of a problem that degree of homogenization affects quality or the like of final products in an emulsion concoction, and non-uniformity of emulsion particles has conventionally not fulfilled sufficient effect.

In addition, a method for producing a Friedel-Crafts type monoalkylation reaction substance in high selectivity, by subjecting an aromatic compound and an alkylating agent to a reaction in a micro-reactor, is also known (JP-A-2004-99443). In this reaction, mixing of 2 miscible liquids in micro-mixer results in rough spreading of relatively large fluid assembly throughout the reactor, turbulent diffusion by vortex, mixing in a gradually finer range, and then rapid progressing of a reaction in micro-space, by which high selectivity is provided.

It should be noted that "a micro-reactor" is a general name of a very small reactor having a micro fluid passage of several to several hundreds μm, having such features as:

(1) high heating and cooling rate (2) laminar flow (3) large surface area per unit volume (4) rapid progress of a reaction due to short diffusion length of a substance

DISCLOSURE OF THE INVENTION

However, the method described in the JP-B-61-28663 makes control of reaction temperature difficult, because of simultaneous generation of heat of dissolution and heat of reaction of hydrogen chloride, in blowing hydrogen chloride gas into acetonitrile. Blowing of hydrogen chloride gas over an extended period of time to control reaction temperature reduces production efficiency and thus unsuitable to industrial operation.

In addition, the method described in the JP-A-2000-191618 requires a large amount of excess alcohol in order to dissolve hydrogen chloride in an amount necessary to a reaction, for example, because solubility of hydrogen chloride dissolving in 1 mole of alcohol at a temperature of 0° C. is 0.48 mole. In addition, dissolution of hydrogen chloride requires cooling, which is disadvantageous in industrial production.

In addition, poor stability of an imide ether hydrochloride against water requires a reaction system to be anhydrous, and thus gaseous hydrochloric acid is used. This in turn requires large reaction volume, which was one factor for decreased production efficiency. As described above, conventional methods had a problem of requirement of excess cooling to improve production efficiency, or low productivity.

The present invention is made in view of the above conventional problems, and it is an object of the present invention to provide a method for producing an imide ether compound safely, efficiently and industrially.

The present inventors have studied the production step of an imide ether compound in detail, and have found that use of a flow reaction device consisting of a mixer and a flow reactor can reduce reaction volume, because of efficient dissolution of a hydrogen halide into an alcohol or a mixed liquid of an alcohol and a nitrile compound, and also reducing reaction time because of rapid progress of a reaction; and adjustment of charging amount of raw materials can produce continuously a compound having molar ratio of charged amount, and thus completed the present invention.

According to the present invention, an imide ether compound, which is solid at normal temperature, can be continuously produced. Moreover, due to use of the flow reaction device consisting of a mixer and a flow reactor, a reaction proceeds according to theoretical amount, and therefore, generation of by-products can be suppressed and a reaction product can be obtained in a short period of time.

The above and other objectives, embodiments and other advantages of the present invention will be clear from the following explanation on preferable embodiments and accompanying drawings.

BEST EMBODIMENTS FOR CARRYING OUT THE INVENTION

Figure 1:
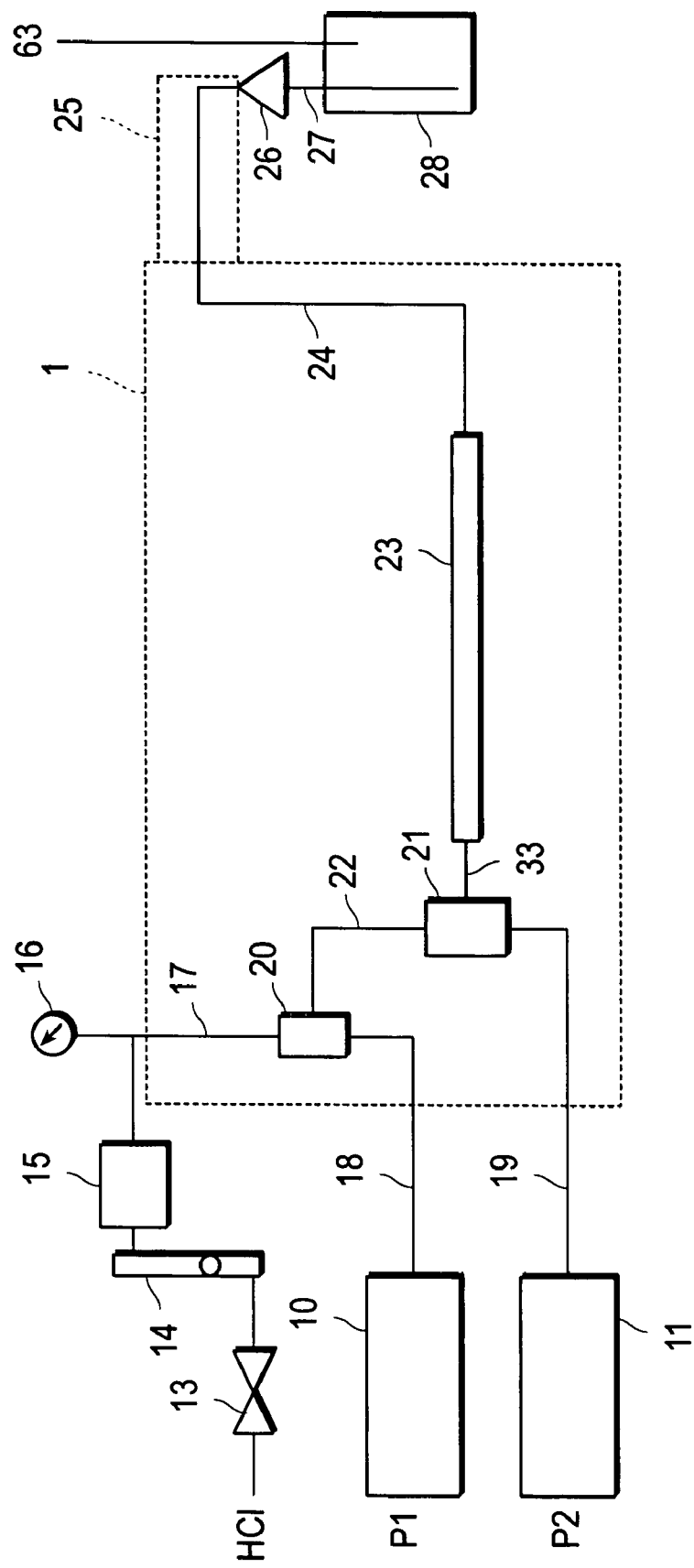
FIG. 1 is a drawing showing an apparatus used in a production method of Examples 1 to 20.

A first aspect of the present invention is a method for producing an imide ether compound represented by the general formula (4), characterized in that a nitrile compound represented by the general formula (1), an alcohol represented by the general formula (2), and a hydrogen halide represented by the general formula (3) are continuously introduced into a flow reaction device comprising a mixer and a flow reactor, to be subjected to a reaction:

(Formula 1)

$$R^1CN \qquad (1)$$

(wherein $R^1$ represents a hydrogen atom, or a C1 to C12 hydrocarbon group or aryl group, which may have a substitution group, or may contain an atom other than carbon in the structure.)

(Formula 2)

$$R^2OH \qquad (2)$$

(wherein $R^2$ represents a C1 to C12 hydrocarbon group.)

(Formula 3)

$$HX \qquad (3)$$

(wherein X represents a chlorine atom, a bromine atom or an iodine atom.)

(Formula 4)

$$R^1C(OR^2)=NH \cdot HX \qquad (4)$$

(wherein $R^1$ represents a hydrogen atom, or a C1 to C12 hydrocarbon group or aryl group, which may have a substitution group, or may contain an atom other than carbon in the structure; $R^2$ represents a C1 to C12 hydrocarbon group; and X represents a chlorine atom, a bromine atom or an iodine atom.)

(1) Raw Material Compounds

In the above general formula (1), $R^1$ represents a hydrogen atom or a C1 to C12 preferably C1 to C8 hydrocarbon group or aryl group, which may have a substitution group, or may contain an atom other than carbon in the structure. As such a hydrocarbon group, a straight or branched alkyl group such as a methyl group, an ethyl group, a n-propyl group, an iso-propyl group, a n-butyl group, an iso-butyl group, a sec-butyl group, a t-butyl group, a n-pentyl group, a n-hexyl group, a n-heptyl group, a n-octyl group, a 2-ethylhexyl group or the like; or cyclic alkyl group such as a cyclopentyl group, a cyclohexyl group or the like is included. In addition, as such an aryl group, a phenyl group, a benzyl group, a phenethyl group, o-, m-, or p-tolyl group, 2,3-, or 2,4-xylyl group, a mesityl group, a naphthyl group, an anthryl group, a phenanthryl group, a biphenylyl group, a benzhydryl group, a trityl group, and pyrenyl group are included. The hydrocarbon group or aryl group may have a substitution group, and an alkoxy group, an alkylthio group, an alkylsilyl group, a carbonyl group, an ester group, an amide group, a nitro group, or a halogen group such as a fluorine atom, a chlorine atom, a bromine atom, and an iodine atom or the like are included. In addition, as the atom, which may be contained in the molecular structure other than a carbon atom, a boron atom, a nitrogen atom, an oxygen atom, and a sulfur atom are included. The substitution group may further have other atom or a substitution group. Specifically, as such a substitution group, a methoxy group, an ethoxy group, a propoxy group, a trifluoromethyl group, a methylthio group, a trimethylsilyl group, a methoxycarbonyl group, an amide group, a hydrogen cyanide group, an acetonitrile group, a propionitrile group, a butyronitrile group, an isobutyronitrile group, a valeronitrile group, an isovaleronitrile group, a pivalonitrile group, a cyclohexane carbonitrile group, a methyl cyanoacetate group, an ethyl cyanoacetate group, a methyl cyanomalonate group, an ethyl cyanomalonate group, a benzonitrile group or the like may be included. It should be noted that because an imide ether compound formed by a reaction is unstable against water, a reaction system preferably be anhydrous as far as possible. As a nitrile compound to be used, an industrial product may be normally used as it is. In the case where a large amount of water is contained, it is preferable that water is removed in advance by distillation or with phosphorus pentoxide, molecular sieve, magnesium sulfate, calcium chloride, sodium sulfate, sodium hydride, calcium hydride or the like.

In an alcohol represented by the above general formula (2), as $R^2$, a C1 to C12 hydrocarbon group, among the above $R^1$, may be preferably used. As such an alcohol, methanol, ethanol, n-propanol, i-propanol, n-butanol, s-butanol, n-heptanol, n-hexanol, n-octanol, 2-ethylhexanol, cyclohexanol, benzyl alcohol or the like are included. In the present invention, methanol, ethanol, n-propanol, i-propanol, n-butanol, s-butanol, cyclohexanol or the like can be suitably used. It should be noted that as an alcohol to be used, an industrial product may be normally used as it is, in the same way as in a nitrile compound. In the case where a large amount of water is contained, it is preferable that water is removed in advance by distillation or with phosphorus pentoxide, molecular sieve, magnesium sulfate, calcium chloride, sodium sulfate, sodium hydride, calcium hydride or the like.

As a hydrogen halide represented by the general formula (3), hydrogen chloride, hydrogen bromide and hydrogen iodide are included. The hydrogen halide is usually used in a normal temperature and normal pressure system, as a gaseous state, however, in a pressurized system equipped with a back-pressure apparatus, it may be used as liquid or a mixture of liquid and gas.

An imide ether compound represented by the general formula (4) is a compound corresponding to the above-described raw material. It is widely used as an intermediate of a medical drug or the like, and a hydrochloric acid salt, a hydrobromic acid salt, and a hydroiodic acid salt of such as methyl formimidate, ethyl formimidate, n-propyl formimidate, i-propyl formimidate, n-butyl formimidate, i-butyl formimidate, n-hexyl formimidate, methyl acetimidate, ethyl acetimidate, n-propyl acetimidate, i-propyl acetimidate, n-butyl acetimidate, i-butyl acetimidate, n-hexyl acetimidate, methyl ethylimidate, ethyl ethylimidate, n-propyl ethylimidate, i-propyl ethylimidate, n-butyl ethylimidate, i-butyl ethylimidate, n-hexyl ethylimidate, methyl n-propylimidate, ethyl n-propylimidate, n-propyl n-propylimidate, propyl n-propylimidate, n-butyl n-propylimidate, i-butyl n-propylimidate, n-hexyl n-propylimidate, methyl i-propylimidate, ethyl i-propylimidate, n-propyl i-propylimidate, i-propyl i-propylimidate, n-butyl i-propylimidate, i-butyl propylimidate, n-hexyl i-propylimidate, methyl n-butylimidate, ethyl n-butylimidate, n-propyl n-butylimidate, i-propyl n-butylimidate, n-butyl n-butylimidate, i-butyl n-butylimidate, n-hexyl n-butylimidate, methyl sec-butylimidate, ethyl sec-butylimidate, n-propyl sec-butylimidate, i-propyl sec-butylimidate, n-butyl sec-butylimidate, i-butyl sec-butylimidate, n-hexyl sec-butylimidate, methyl cyclohexylimidate, ethyl cyclohexylimidate, n-propyl cyclohexylimidate, i-propyl cyclohexylimidate, n-butyl cyclohexylimidate, butyl cyclohexylimidate, n-hexyl cyclohexylimidate, methyl methoxycarbonylmethylimidate, ethyl methoxycarbonylmethylimidate, n-propyl methoxycarbonylmethylimidate, i-propyl methoxycarbonylmethylimidate, n-butyl methoxycarbonylmethylimidate, butyl methoxycarbonylmethylimidate, n-hexyl methoxycarbonylmethylimidate, methyl methoxycarbonylethylimidate, ethyl methoxycarbonylethylimidate, n-propyl methoxycarbonylethylimidate, propyl methoxycarbonylethylimidate, n-butyl methoxycarbonylethylimidate, butyl methoxycarbonylethylimidate, n-hexyl methoxycarbonylethylimidate, methyl methylmalonylimidate, ethyl methylmalonylimidate, n-propyl methylmalonylimidate, i-propyl methylmalonylimidate, n-butyl methylmalonylimidate, i-butyl methylmalonylimidate, n-hexyl methylmalonylimidate, methyl ethylmalonylimidate, ethyl ethylmalonylimidate, n-propyl ethylmalonylimidate, i-propyl ethylmalonylimidate, n-butyl ethylmalonylimidate, i-butyl ethylmalonylimidate, n-hexyl ethylmalonylimidate, methyl phenylimidate, ethyl phenylimidate, n-propyl phenylimidate, i-propyl phenylimidate, n-butyl phenylimidate, i-butyl phenylimidate, n-hexyl phenylimidate or the like can be produced.

(2) A Flow Reaction Device

A structure of a flow reaction device used in the present invention is not especially limited as long as including a mixer and a flow reactor, and providing a reaction apparatus of a type that fluid is continuously flown in, reacted and flown out after reaction from a reaction system.

As a flow reactor, which may be used in a flow reaction device in the present invention, one having an inlet, a reaction unit (hereafter may be referred to as a reaction unit of a flow reactor) and an outlet may be widely used. In addition, as the reaction unit of the flow reactor, any one may be used as long as having a shape which can flow and react continuously the mixed liquid, which is raw material liquid mixed by the mixer and is introduced from the introduction unit, for example, circular tube, angular tube, elliptic tube like one may be accepted. Furthermore, the reaction unit may equip internally a mixing unit (hereafter may be referred to as a mixing unit of a flow reactor) having function to enable to mix continuously 2 or more kinds of fluids such as gas and liquid, or liquid and liquid. As such a flow reactor, for example, a Y-shaped type reactor, a T-shaped type reactor, a cross type reactor, a pipeline type reactor having static mixing function internally, or a screw feeder type reactor having driving type mixing function internally, and furthermore a micro-reactor disclosed in the above JP-A-2004-99443 may be suitably used. More preferably, use of a flow reaction device installed with a temperature control unit is capable of providing safer reaction, because temperature control inside the reaction apparatus becomes easy. As such a flow reaction device, a reaction apparatus of such as spiral type, core-and-shell type, plate heat exchange type or the like may be used. Equivalent diameter of a reaction unit of a flow reactor used in the present invention may be selected as appropriate depending on a reaction system or kinds of raw materials, however, it is 10 to 300,000 μm, more preferably 50 to 200,000 μm. The equivalent diameter below 10 μm is disadvantageous due to requirement of high pressure in transferring of reaction liquid; on the other hand, the equivalent diameter over 300,000 μm is not preferable due to occurrence of drift. Flow amount in the reactor is related to reaction rate, and thus may be selected as appropriate depending on reaction rate, and flow rate in the reactor used in the above reaction is set so that a residence time (reaction time) of preferably equal to or less than 10,000 seconds, more preferably equal to or less than 5,000 seconds, and particularly preferably equal to or less than 1,000 seconds is attained. In addition, material of the reactor is preferably one not to be impinged by raw material substances and, for example, a metal (various alloys of titanium, nickel, or Hastelloy C), a resin (a fluorine resin), glass, porcelain (cordierite, ceramics) are included.

In the meantime, as a mixer, which may be used in the above flow reaction device, one having an inlet, a mixing unit (hereafter may be referred to as a mixing unit of a mixer) and an outlet may be widely used.

As such a mixing unit of a mixer, any one may be adopted as long as having function to enable to mix continuously 2 or more kinds of fluids such as gas and liquid, or liquid and liquid. As such a mixer having static mixing function, for example, a Y-shaped type reactor, a T-shaped type reactor, a cross type reactor, a pipeline type reactor, or as a mixer having driving type mixing function, a screw feeder type reactor and furthermore also a micro-reactor disclosed in the above JP-A-2004-99443 may be suitably used as the above mixer. In the present invention, equivalent diameter of the mixing unit of the mixer may be selected as appropriate depending on a reaction system or kinds of raw materials, however, it is 10 to 300,000 μm, more preferably 50 to 200,000 μm. The equivalent diameter below 10 μm is disadvantageous due to high pressure is required in transferring of reaction liquid; on the other hand, the equivalent diameter over 300,000 μm is not preferable due to resulting in decreased mixing efficiency.

Fundamentally, in a reaction to get an imide ether compound, 1 mole of an imide ether compound is synthesized by 1 mole of alcohol and 1 mole of hydrogen halide, relative to 1 mole of a nitrile compound, as shown by the following formula:

(Formula 5)

$$R^1CN + R^2OH + HX \rightarrow R^1C(OR^2)=NH \cdot HX$$

However, conventional methods generate, in addition to objective substance $R^1C(OR^2)=NH \cdot HX$, by-products such as an ester compound ($R^1COOR^2$) obtained by hydrolysis of an imide ether compound by water co-present in a reaction system, an amide compound ($R^1CONH_2$) as a decomposed by-product of an imide ether compound, and a triazine compound or a hexahydrotriazine compound as a cyclization by-product of an alkyl halide ($R^2X$) and a nitrile compound and the like. In addition, it is required to remove heat of dissolution of hydrogen halide in an alcohol, and further heat of reaction in imide etherification in order to carry out safely imidation. A conventional batch type reactor is poor in heat removal efficiency, therefore, in order to control reaction temperature, after carrying out the step for dissolving hydrogen halide in an alcohol in advance, a nitrile compound is further batch-wise added over a long period of time to be subjected to a reaction (JP-A-2000-191618), or after charging a nitrile compound and an alcohol all at once, a hydrogen halide is introduced over a long period of time to be subjected to a reaction (JP-B-61-28663). In this way, carrying out a reaction over a long period of time may decompose the generated imide ether compound, or by-produce cyclic compounds of a nitrile compound. However, use of a flow reaction device installed with a mixing unit of a mixer having proper equivalent diameter and a reaction unit of a flow reactor having proper equivalent diameter and further preferably a temperature control means is capable of suppressing generation of the above by-products. It is because raw materials can be easily mixed and a reaction proceeds rapidly, due to short diffusion distance inside the mixing unit of a mixer or the reaction unit of a flow reactor having proper equivalent diameter. Use of such a flow reaction device is capable of providing high heat removal efficiency of a flow reaction device and a safe reaction, even in continuous supplying of raw materials. In the case where a reaction is carried out in a pressurized state by installment of a backpressure apparatus at the exit of a gas-liquid mixing type mixer and a flow reactor, solubility of an hydrogen halide to be introduced into an alcohol or a mixed liquid of an alcohol and a nitrile compound is improved, resulting in further rapid progress of a reaction, and it is particularly preferable.

(3) A Reaction Pattern A

In the present invention, an imide ether compound can be produced by adjustment of introducing ratio of the alcohol into the flow reaction device to be 0.5 to 3.0 moles, more preferably 0.7 to 2.0 moles, and particularly preferably 0.9 to 1.5 moles, relative to 1 mole of the nitrile compound mentioned above. The alcohol below 0.5 moles, relative to 1 mole of the nitrile compound, is disadvantageous due to providing low conversion rate of the nitrile. On the other hand, the alcohol over 3.0 moles is disadvantageous due to providing slow reaction and decreased productivity. In addition, an imide ether compound can be produced by adjustment of ratio of the hydrogen halide to be 0.5 to 3.0 moles, more preferably 0.7 to 2.0 moles, and particularly preferably 0.9 to 1.5 moles, relative to 1 mole of the nitrile compound. The hydrogen halide below 0.5 mole is disadvantageous due to providing low conversion rate of the nitrile. On the other hand, the hydrogen halide over 3.0 moles is economically disadvantageous due to increase in production cost. As described above, 1 mole of the imide ether compound is stoichiometrically synthesized by 1 mole of an alcohol and 1 mole of hydrogen halide, relative to 1 mole of a nitrile compound, however, in the present invention, due to use of a flow reaction device, generation of by-products can be suppressed by the following reasons, even when raw materials are continuously introduced in the above ratio: 1. Reaction rate is high; 2. Reaction temperature can be controlled; and 3. Residence time of reaction liquid in a flow reactor can be adjusted arbitrarily; and the like.

In the present invention, as for introduction order of the nitrile compound, the alcohol and the hydrogen halide, the following methods may be adopted, in the case where inlets for only 2 kinds of fluids are present in the second mixer (21) of a flow reaction device, for example, as shown in FIG. 1: 1. A method for supplying and mixing the alcohol and the hydrogen halide in advance into the first mixer (20), followed by continuously supplying and mixing the resultant mixture and the nitrile compound and then continuously introducing them into the flow reactor (23) to be subjected to a reaction in the reaction unit of the flow reactor; and 2. A method for supplying and mixing the nitrile compound and the alcohol in advance in the first mixer, followed by continuously supplying and mixing the resultant mixture and the hydrogen halide into the second mixer, and then continuously introducing them into the flow reactor to be subjected to a reaction in the reaction unit of the flow reactor, although different from that shown in FIG. 1. For example, in the case where inlets for 3 kinds of fluids are present in the mixer of a flow reaction device, a method for simultaneously supplying and mixing the nitrile compound, the alcohol and the hydrogen halide into a mixer, and then continuously introducing them into the flow reactor to be subjected to a reaction, may be adopted. In the present invention, conversion ratio of the nitrile compound over 75% causes precipitation of the imide ether compound as solid and makes reaction liquid to a slurry state, which raises a clogging problem by the slurry in the reaction unit of the flow reactor. As a method for preventing the clogging, the following methods can be adopted: 1. Equivalent diameter of the reaction unit of the flow reactor is made larger than diameter of the imide ether compound precipitating as solid; 2. A difficult-to-clog shape is designed so that the reaction unit of the flow reactor has a flow passage width of certain size; 3. Reaction liquid is discharged from the reaction unit of the flow reactor before conversion rate of the nitrile compound is over 75%, and the reaction liquid and a solvent not affecting the reaction are continuously introduced into the second flow reactor, which will be described later; and 4. Reaction liquid is discharged from the reaction unit of the flow reactor before conversion rate of the nitrile compound is over 75%, and the reaction liquid and a solvent not affecting the reaction are subjected to a reaction using a batch type reactor. It should be noted that, as the solvent not affecting the reaction liquid and the reaction, an aliphatic hydrocarbon such as pentane, hexane, heptane, octane, cyclohexane, methylcyclohexane, normal paraffin or the like; an aromatic hydrocarbon such as benzene, toluene, xylene, mesitylene, durene or naphthalene or the like; or the like are included.

In the reaction pattern A, equivalent diameter of the mixing unit of the mixer is 10 to 300,000 μm, preferably 100 to 200,000 μm and particularly preferably 500 to 100,000 μm. The equivalent diameter below 10 μm is disadvantageous because high pressure is required in introduction of raw material liquid, on the other hand, the equivalent diameter over 300,000 μm is not preferable because mixing efficiency is decreased.

In addition, equivalent diameter of the reaction unit of the flow reactor to be used in the present invention is 50 to 300,000 μm, preferably 100 to 300,000 μm and particularly preferably 500 to 200,000 μm. The equivalent diameter below 50 μm is disadvantageous due to incurring clogging of the reactor by slurry of the imide ether compound, requiring high pressure in introducing raw material liquid or, in some cases, clogging the flow passage of the flow reactor by slurry of the imide ether compound, on the other hand, the equivalent diameter over 300,000 μm is not preferably due to generation of drift.

In addition, in the case where the reaction is carried out in a pressurized state by installment of a backpressure apparatus at the exit of the mixer or the flow reactor, solubility of the introduced hydrogen halide into the alcohol is improved, resulting in further rapid progress of the reaction. In the present invention, the reaction by the alcohol, the nitrile compound and the hydrogen halide in the flow reactor is generally carried out under control of temperature of reaction liquid at −10 to 150° C., preferably 0 to 120° C. and particularly preferably 0 to 100° C. The temperature below −10° C. is disadvantageous due to providing extremely low reaction rate. On the other hand, the temperature over 150° C. is disadvantageous because suppression of by-product generation becomes impossible. Reaction pressure of the alcohol, the nitrile compound and the hydrogen halide in the flow reaction device, at least in the reaction unit of the flow reactor, may be adjusted to be 0.05 to 100 MPa, preferably 0.1 to 10 MPa, and particularly preferably 0.2 to 5 MPa. In addition, reaction time, namely residence time in a flow reactor, is not limited, but is generally 0.1 to 10000 seconds, preferably 1 to 5000 seconds and particularly preferably 5 to 1000 seconds, however, it may be set as appropriate depending on reaction rate.

(4) A Reaction Pattern B

In the present invention, an imide ether compound can also be produced by continuously introducing the nitrile compound mentioned above, the alcohol in a ratio of 0.3 to 0.7 mole, and the hydrogen halide in a ratio of 0.8 to 3.0 moles, relative to 1 mole of the nitrile compound mentioned above, into the first flow reaction device composed of a mixer and a flow reactor, and then by continuously introducing reaction liquid containing the resultant imide ether compound, and the alcohol in a ratio that total amount of the alcohol is 1.0 to 3.0 moles relative to 1 mole of the nitrile compound, into the second flow reactor to be subjected to a reaction. In this way, namely by the divided addition of the alcohol required in the reaction, heat of reaction generating during the reaction is dividedly removed and a safer reaction method is attained. For example, in the first flow reaction device, 0.3 to 0.7 moles of the alcohol, preferably 0.4 to 0.6 moles, and 0.8 to 3.0 moles of the hydrogen halide, preferably 0.9 to 2.0 moles and particularly preferably 1.0 to 1.5 moles, relative to 1 mole of the nitrile compound, are subjected to a reaction in the first flow reaction device, and then into reaction liquid containing the resultant imide ether compound, the alcohol is continuously introduced into the second flow reactor in a ratio that total amount of the alcohol to be used is 1.0 to 3.0 moles, preferably 1.05 to 2.0 moles and particularly preferably 1.1 to 1.5 moles, relative to 1 mole of the nitrile compound, to complete the reaction. The ratio of the alcohol below 1.0 mole, relative to 1 mole of the nitrile compound, is disadvantageous because unreacted nitrile compounds are left. On the other hand, the ratio of the alcohol over 3.0 moles is disadvantageous due to providing low reaction rate and decreased productivity. The imide ether compound can be produced even in the first stage, however, the imide ether compound will not precipitate in reaction liquid as long as the ratio is within the above range. Then, in the second stage, by the addition of the alcohol into unreacted raw materials contained in reaction liquid, conversion rate of the nitrile compound is improved, and thus the imide ether compound can be efficiently produced. In this case, because the imide ether compound becomes a solid state and precipitates, and makes reaction liquid to a slurry state, with the addition of the alcohol, a clogging problem in the second flow reactor is raised. As a method for preventing the clogging, the following methods can be adopted: 1. A solvent not affecting the reaction is introduced in the addition of the alcohol; and 2. Equivalent diameter of the reaction unit of the second flow reactor is made larger than diameter of the reaction unit of the flow reactor of the first flow reaction device. It should be noted that the second flow reactor used in the present invention may be the second flow reaction device further having a mixer.

Figure 2:
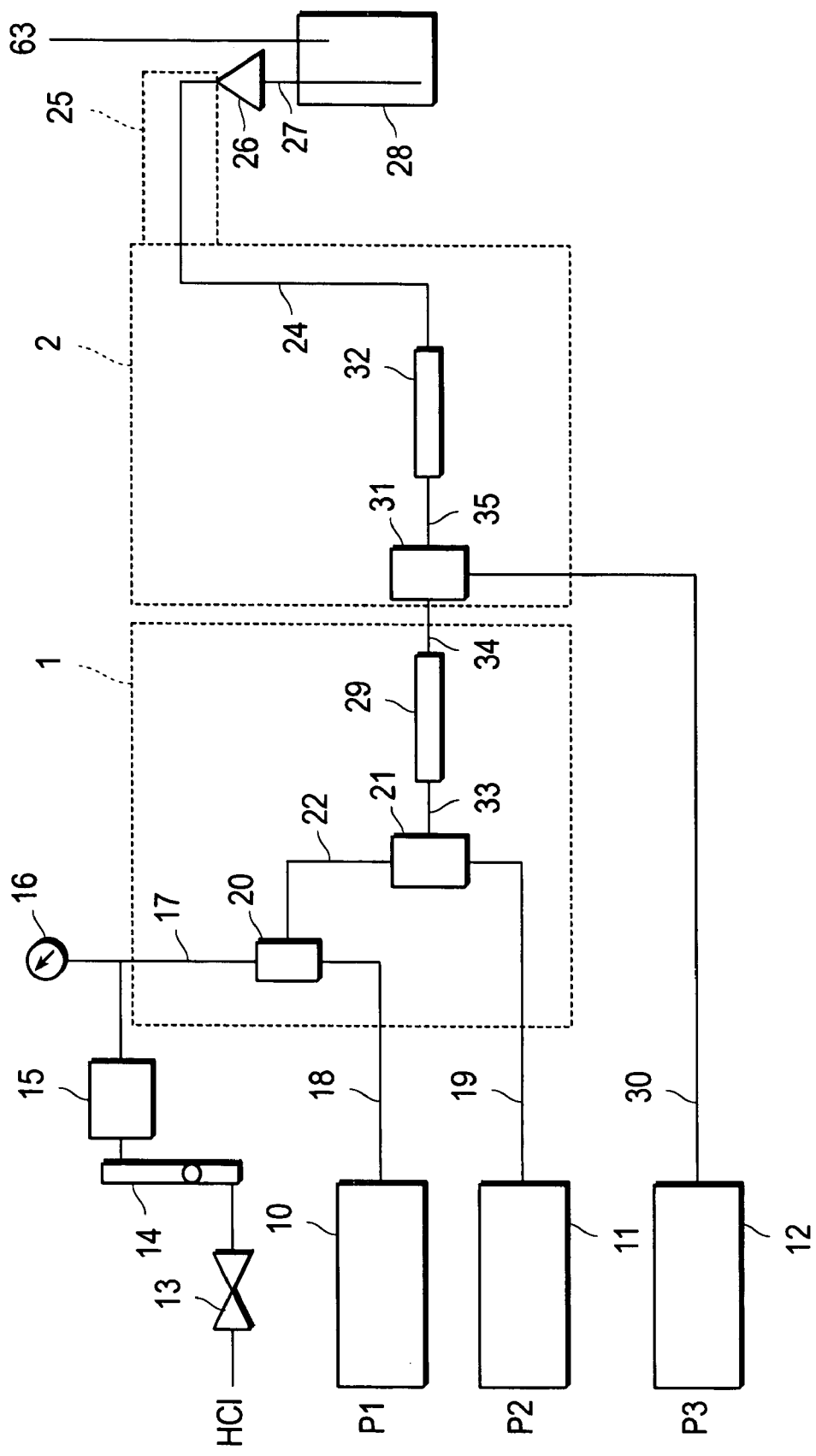
FIG. 2 is a drawing showing an embodiment of the present invention.

In the present invention, as for introduction order of the nitrile compound, the alcohol and the hydrogen halide is not especially limited. For example, in the case where inlets for only 2 kinds of fluids are present in the second mixer (21) of the first flow reaction device, as shown in FIG. 2, the following method may be adopted; 1. A method for supplying and mixing the alcohol and the hydrogen halide in advance into the first mixer (20) of the first flow reaction device, followed by supplying and mixing the resultant mixture and the nitrile compound into the second mixer (21), then continuously introducing them into the first flow reactor (29) to be subjected to a reaction in the reaction unit of the first flow reactor, and then supplying and mixing reaction liquid containing an imide ether compound discharged from the first flow reaction device, and a solvent into a mixer (not shown), supplying and mixing the resultant mixture and the alcohol into the mixer (31) of the second flow reaction device, and then continuously introducing them into the second flow reactor (32) to be subjected to a reaction in the reaction unit of the second flow reactor. Although it is different from FIG. 2, in the case where the first flow reactor and the second flow reactor have function, internally, to mix 2 kinds of fluids, the following methods may be adopted; 2. A method for supplying and mixing the alcohol and the hydrogen halide in advance into the mixer of the first flow reaction device, followed by continuously introducing the resultant mixed liquid and the nitrile compound into the first flow reactor to be subjected to a reaction in the reaction unit of the first flow reactor, and then supplying and mixing reaction liquid containing an imide ether compound discharged from the first flow reaction device, and a solvent not affecting the reaction into a mixer of the second flow reaction device, and then continuously introducing the resultant mixture and the alcohol into the second flow reactor, to be subjected to a reaction in the reaction unit of the second flow reactor; 3. A method for supplying and mixing the alcohol and the hydrogen halide in advance into the mixer of the first flow reaction device, followed by continuously introducing the resultant mixed liquid and the nitrile compound into the first flow mixer to be subjected to a reaction in the reaction unit of the first flow reactor, and then supplying and mixing reaction liquid containing an imide ether compound discharged from the first flow reaction device, and the alcohol into a mixer of the second flow reaction device, and then continuously introducing the resultant mixed liquid, and a solvent not affecting the reaction into the second flow reactor, to be subjected to a reaction in the reaction unit of the second flow reactor. Further, 4. A method for supplying and mixing the nitrile compound and the alcohol in advance into the mixer of the first flow reaction device, followed by continuously introducing the resultant mixture and the hydrogen halide into the first flow reactor to be subjected to a reaction in the reaction unit of the first flow reactor, and then continuously introducing reaction liquid containing an imide ether compound discharged from the first flow reaction device, and the alcohol into the second flow reactor, to be subjected to a reaction in the reaction unit of the second flow reactor; 5. A method for supplying and mixing the nitrile compound and the alcohol in advance into the mixer of the first flow reaction device, followed by continuously introducing the resultant mixture and the hydrogen halide into the first flow reactor, to be subjected to a reaction in the reaction unit of the first flow reactor, and then supplying and mixing reaction liquid containing an imide ether compound discharged from the first flow reaction device, and a solvent not affecting the reaction into the mixer of the second flow reaction device, and then continuously introducing the resultant mixed liquid and the alcohol into the second flow reactor, to be subjected to a reaction in the reaction unit of the second flow reactor; and 6. A method for supplying and mixing the nitrile compound and the alcohol in advance into the mixer of the first flow reaction device, followed by continuously introducing the resultant mixed liquid and the hydrogen halide into the first flow reactor, to be subjected to a reaction in the reaction unit of the first flow reactor, and then supplying and mixing reaction liquid containing an imide ether compound discharged from the first flow reaction device, and the alcohol into the mixer of the second flow reaction device, and then continuously introducing the resultant mixed liquid, and a solvent not affecting the reaction into the second flow reactor, to be subjected to a reaction in the reaction unit of the second flow reactor.

It should be noted that, for example, in the case where the first mixer has inlets for 3 kinds of fluids, a method may be adopted for continuously introducing the nitrile compound, the alcohol and the hydrogen halide at the same time to the first flow reaction device, to be subjected to a reaction, and introducing an imide ether compound discharged from the first flow reaction device, the alcohol, and a solvent not affecting the reaction into the second flow reactor, to be subjected to a reaction.

Equivalent diameter of the reaction unit of the mixer of the first flow reaction device to be used in the present invention is 10 to 300,000 μm, preferably 100 to 200,000 μm and particularly preferably 500 to 100,000 μm. The equivalent diameter below 10 μm is disadvantageous, because high pressure is required in introduction of raw material liquid, on the other hand, the equivalent diameter over 300,000 μm is not preferable because mixing efficiency is decreased. In addition, equivalent diameter of the reaction unit of the flow reactor of the first flow reaction device to be used in the present invention is 10 to 300,000 μm, preferably 100 to 200,000 μm and particularly preferably 500 to 100,000 μm. The equivalent diameter below 10 μm is disadvantageous, because high pressure is required in transfer of reaction liquid, on the other hand, the equivalent diameter over 300,000 μm is not preferable because drift is generated. In addition, equivalent diameter of the reaction unit of the second flow reactor to be used in the present invention may be designed larger than diameter of an imide ether compound precipitating as solid, and is 50 to 300,000 μm, preferably 100 to 200,000 μm and particularly preferably 500 to 100,000 μm. The equivalent diameter below 50 μm is disadvantageous, because slurry of the imide ether compound may clog the second flow reaction device, or high pressure is required in introducing reaction liquid, on the other hand, the equivalent diameter over 300,000 μm is not preferable because drift is generated.

In addition, in the case where the reaction is carried out in a pressurized state by installment of a backpressure apparatus at the exit of the first flow reaction device, solubility of the hydrogen halide introduced to the alcohol is improved, resulting in further rapid progress of the reaction. On the other hand, in the case where a method for supplying the nitrile compound and the hydrogen halide in advance into the reactor, or a method for direct introduction to the reaction unit of the flow reactor is adopted, because a reaction product between the nitrile compound and the hydrogen halide is solid, the method may incur clogging of the mixer or the flow reactor.

It is preferable to control reaction in the first stage to be carried out at −10 to 150° C., preferably 0 to 120° C., and particularly preferably 10 to 100° C., however, because of small quantity of heat of reaction due to small introduction amount of the alcohol, control of temperature within the above range is easy. In addition, because of small generation amount of the imide ether compound, which is solid at normal temperature, due to small introduction amount of the alcohol, it is easy to adjust so as not to generate slurry at the first stage. The reaction temperature below −10° C. is disadvantageous due to providing extremely low reaction rate. On the other hand, the temperature over 150° C. is disadvantageous because suppression of by-product generation becomes impossible. Reaction pressure in the first stage may be adjusted to be 0.05 to 100 MPa, preferably 0.1 to 10 MPa, and particularly preferably 0.2 to 5 MPa. A reaction in the second stage is preferably controlled at −10 to 150° C., preferably 0 to 120° C., and particularly preferably 10 to 100° C., however, because of small quantity of heat of reaction due to no introduction of new hydrogen halide at the second stage, control of the temperature within the above range is easy. The reaction temperature below −10° C. is disadvantageous due to providing extremely low reaction rate. On the other hand, the reaction temperature over 150° C. is disadvantageous because suppression of by-product generation becomes impossible. Reaction pressure in the second flow reaction device is not limited, however, the reaction is desirably carried out under normal pressure. In addition, reaction time, namely residence time in the first and the second flow reaction devices, is not limited, but is generally 0.1 to 10,000 seconds, preferably 1 to 5,000 seconds and particularly preferably 5 to 1,000 seconds, however, it may be set as appropriate depending on reaction rate.

(5) A Reaction Pattern C

Figure 3:
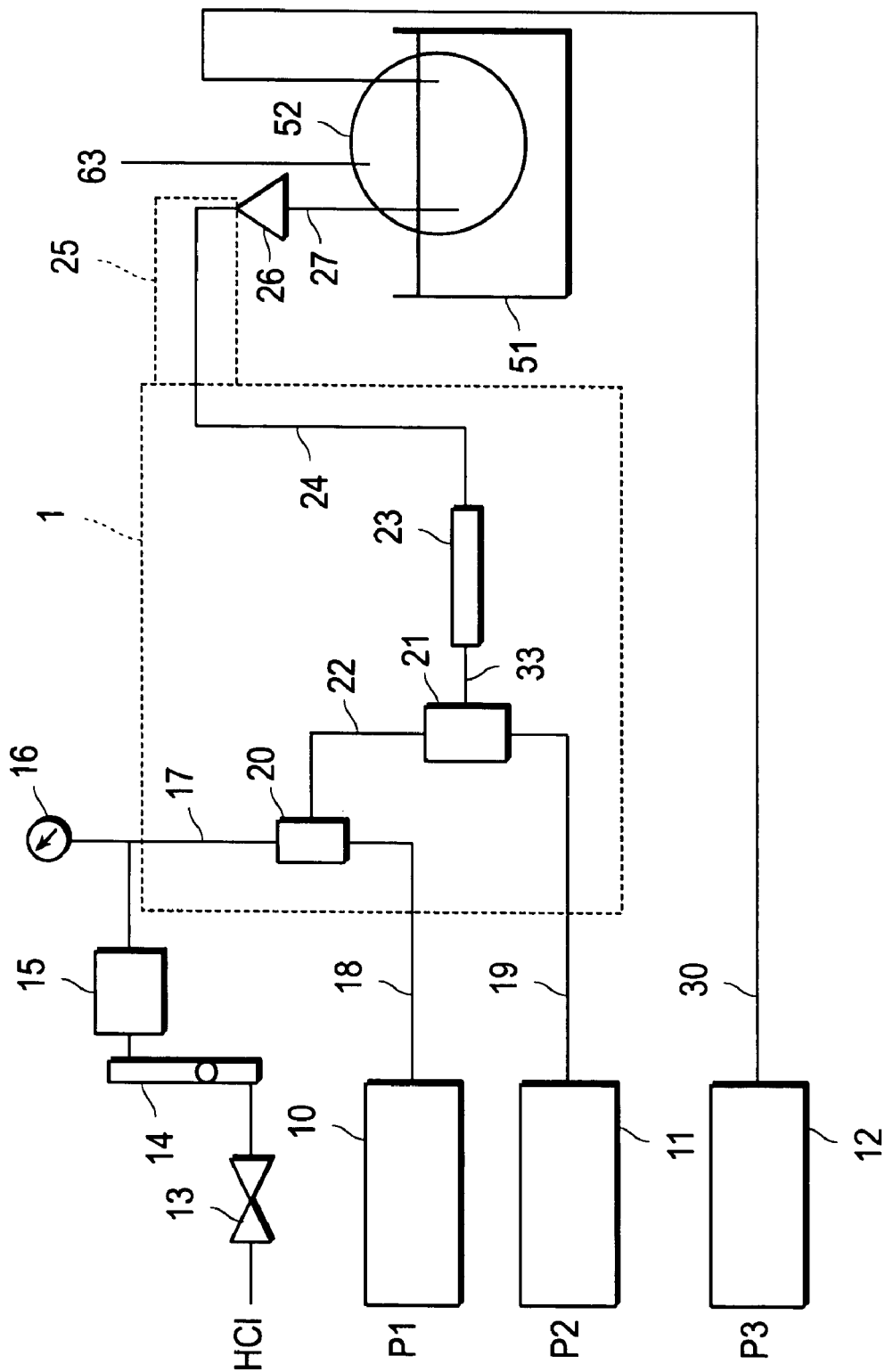
FIG. 3 is a drawing showing an apparatus used in a production method of Example 21.

In the present invention, after obtaining reaction liquid containing the imide ether compound by continuously introducing the alcohol mentioned above in a ratio of 0.3 to 0.7 mole, and the hydrogen halide mentioned above in a ratio of 0.8 to 3.0 moles, relative to 1 mole of the nitrile compound mentioned above, into the flow reaction device, the reaction liquid mentioned above may be subjected to a reaction with the alcohol in a ratio that total amount of the alcohol is 1.0 to 3.0 moles, relative to 1 mole of the nitrile compound mentioned above. For example, as shown in FIG. 3, 0.3 to 0.7 moles of the alcohol, preferably 0.4 to 0.6 moles, and 0.8 to 3.0 moles of the hydrogen halide, preferably 0.9 to 2.0 moles and particularly preferably 1.0 to 1.5 moles, relative to 1 mole of the nitrile compound, are continuously introduced to the flow reaction device to be subjected to a reaction, to obtain reaction liquid containing an imide ether compound, and then the reaction liquid mentioned above and the alcohol mentioned above is introduced into a batch type reactor in a ratio that total amount of the alcohol to be used is 1.0 to 3.0 moles, preferably 1.05 to 2.0 moles and particularly preferably 1.1 to 1.5 moles, relative to 1 mole of the nitrile compound, to complete the reaction, and thus the imide ether compound can be efficiently produced. The ratio of the alcohol below 1.0 mole, relative to 1 mole of the nitrile compound, is disadvantageous because unreacted nitrile compounds are left. On the other hand, the ratio of the alcohol over 3.0 moles is disadvantageous due to providing low reaction rate and decreased productivity. According to this method, the imide ether compound can be produced in the first stage, however, because the imide ether compound will not precipitate in reaction liquid as long as the ratio is within the above range, there is no clogging problem in the mixer and the flow reactor.

Equivalent diameter of the mixing unit of the mixer used in the present invention is 10 to 300,000 μm, preferably 100 to 200,000 μm and particularly preferably 500 to 100,000 μm. The equivalent diameter below 10 μm is disadvantageous because high pressure is required in introduction of raw material liquid, the equivalent diameter over 300,000 μm is not preferable because mixing efficiency is decreased. On the other hand, equivalent diameter of the reaction unit of the flow reactor is 10 to 300,000 μm, preferably 100 to 200,000 μm and particularly preferably 500 to 100,000 μm. The equivalent diameter below 10 μm is disadvantageous because high pressure is required in introduction of raw material liquid, on the other hand, the equivalent diameter over 300,000 μm is not preferable because drift is generated.

Reaction temperature in the flow reactor is preferably controlled to be −10 to 150° C., preferably 0 to 120° C. and particularly preferably 10 to 100° C. The temperature below −10° C. is disadvantageous due to providing extremely low reaction rate. On the other hand, the temperature over 150° C. is disadvantageous because suppression of by-product generation becomes impossible. Reaction pressure in the flow reactor is not limited, however, it is preferably adjusted so that backpressure is 0.05 to 100 MPa, preferably 0.1 to 10 MPa, and particularly preferably 0.2 to 5 MPa. In addition, reaction time, namely residence time in the flow reactor, is not limited, but is generally 0.1 to 10,000 seconds, preferably 1 to 5,000 seconds and particularly preferably 5 to 1,000 seconds, however, it may be set as appropriate depending on reaction rate.

(6) A Reaction Pattern D

Figure 4:
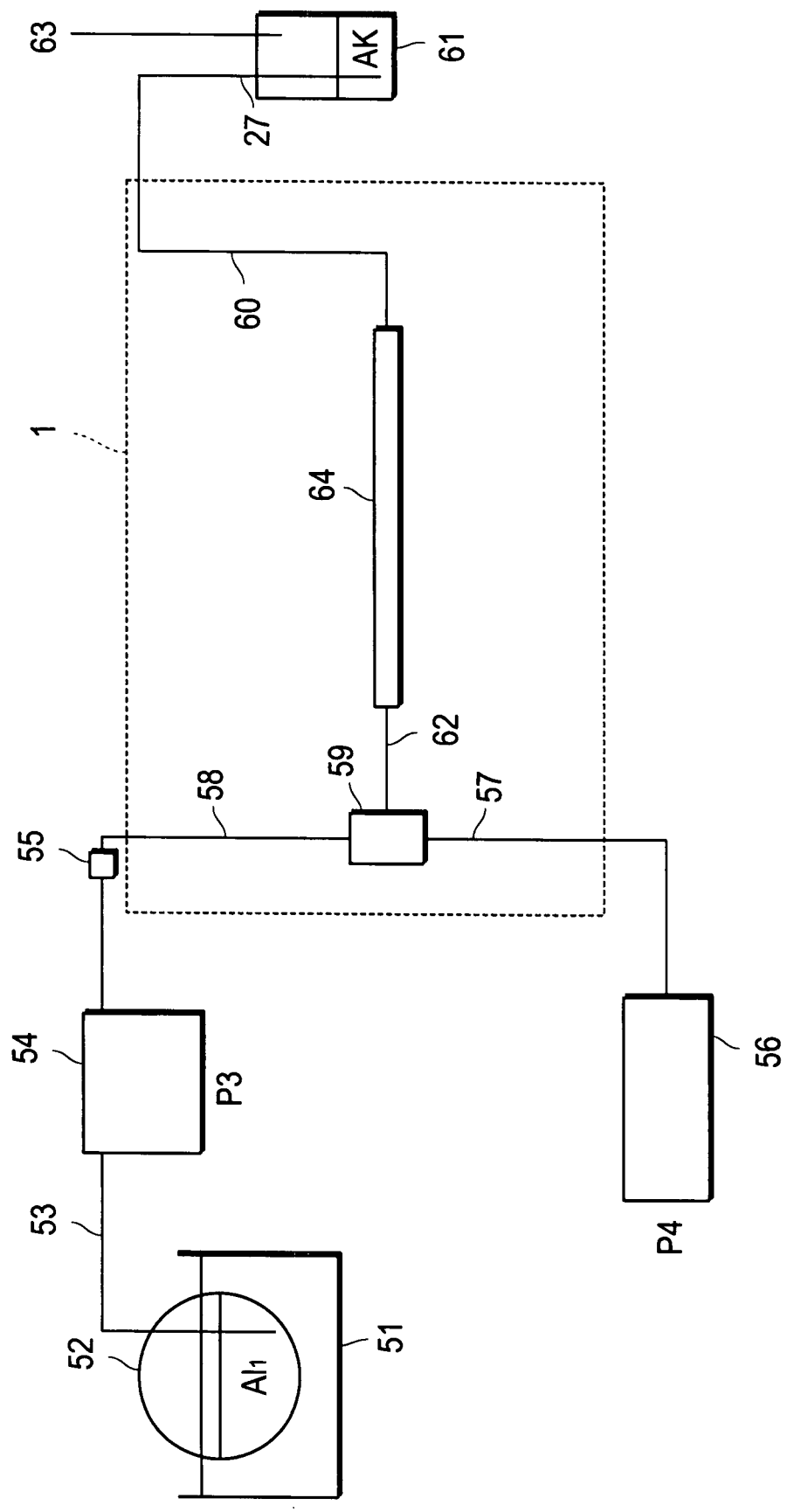
FIG. 4 is a drawing showing an apparatus used in a production method of Example 22.

In the present invention, after obtaining reaction liquid containing an imide ether compound obtained by subjecting the nitrile compound mentioned above and the alcohol in a ratio of 0.3 to 0.7 mole, and the hydrogen halide in a ratio of 0.8 to 3.0 moles, relative to 1 mole of the nitrile compound, to a reaction; the reaction liquid, and the alcohol in a ratio that total amount of the alcohol to be used is 1.0 to 3.0 moles, relative to 1 mole of the nitrile compound, may be continuously introduced into the flow reactor having a mixer and a flow reactor, to be subjected to a reaction. For example, as shown in FIG. 4, according to a conventionally known method, the alcohol in a reduced ratio of 0.3 to 0.7 mole, preferably 0.4 to 0.6 mole, and the hydrogen halide in a ratio of 0.8 to 3.0 moles, preferably 0.9 to 2.0 moles and particularly preferably 1.0 to 1.5 moles, relative to 1 mole of the nitrile compound, are subjected to a reaction, to obtain reaction liquid containing the imide ether compound, and then the reaction liquid and the alcohol are continuously introduced into the flow reactor 64 in ratio of the alcohol so that total amount of the alcohol to be used is 1.0 to 3.0 moles, preferably 1.05 to 2.0 moles and particularly preferably 1.1 to 1.5 moles, relative to 1 mole of the nitrile compound, to complete the reaction, and thus the imide ether compound can be efficiently produced. The ratio of the alcohol below 1.0 mole, relative to 1 mole of the nitrile compound, is disadvantageous because unreacted nitrile compounds are left. On the other hand, the ratio of the alcohol over 3 moles is disadvantageous due to providing low reaction rate and decreased productivity. In this case, with the addition of the alcohol, the imide ether compound precipitates and makes a slurry state, however, a method for prevention described in the reaction pattern B may be adopted to prevent clogging of the flow reactor by the slurry. This method does not require vapor-liquid mixing, and is capable of producing the imide ether compound using only a flow reactor of a liquid-liquid mixing type, and thus is advantageous.

Equivalent diameter of the mixing unit of the mixer used in the present invention is 50 to 300,000 μm, preferably 200 to 200,000 μm and particularly preferably 500 to 100,000 μm. The equivalent diameter below 50 μm is disadvantageous because high pressure is required in introduction of raw material liquid, or slurry of the imide ether compound may sometimes clog the flow passage of the flow reactor, on the other hand, the equivalent diameter over 300,000 μm is not preferable because mixing efficiency is decreased.

Equivalent diameter of the reaction unit of the flow reactor to be used in the present invention is 50 to 300,000 μm, preferably 200 to 200,000 μm and particularly preferably 500 to 100,000 μm. The equivalent diameter below 50 μm is disadvantageous due to requiring high pressure in introducing raw material liquid, on the other hand, the equivalent diameter over 300,000 μm is not preferably due to generation of drift.

Reaction temperature in the flow reactor is preferably controlled to be −10 to 150° C., preferably 0 to 120° C. and particularly preferably 10 to 100° C., however, because heat generation amount is small due to no introduction of new hydrogen halide into the flow reaction device, control of the temperature within the range mentioned above is easy. The temperature below −10° C. is disadvantageous due to providing extremely low reaction rate. On the other hand, the temperature over 150° C. is disadvantageous because suppression of by-product generation becomes impossible. Reaction pressure in the flow reactor is not limited, however, the reaction is desirably carried out under normal pressure. In addition, reaction time, namely residence time in the flow reactor, is not limited, but is generally 0.1 to 10,000 seconds, preferably 1 to 5,000 seconds and particularly preferably 5 to 1,000 seconds, however, it may be set as appropriate depending on reaction rate.

EXAMPLES

The present invention will specifically be described below with reference to Examples, however, the present invention should not be limited to these Examples.

Examples 1 to 11

A methyl acetimidate hydrochloride was produced by using an apparatus shown in FIG. 1.

To the inlet of the first mixer (a 3-way union, produced by Swagelok Co., Ltd.) 20, the Teflon (Registered Trademark) tube (an inner diameter of 0.5 mm and an outer diameter of 1/16 inch) 17 for introducing hydrogen chloride gas, and the Teflon (Registered Trademark) tube (an inner diameter of 0.5 mm and an outer diameter of 1/16 inch) 18, which was connected to a liquid feed pump (produced by Shimadzu Corp.) 10 for supplying methanol, were connected, and to the outlet, the Teflon (Registered Trademark) tube (an inner diameter of 0.5 mm and an outer diameter of 1/16 inch) 22 was connected. To the inlet of the second mixer (a 3-way union, produced by Swagelok Co., Ltd.) 21, the Teflon (Registered Trademark) tube 22, and the Teflon (Registered Trademark) tube 19, which was connected to a liquid feed pump (produced by Shimadzu Corp.) 11 for supplying acetonitrile, were connected, and to the outlet, the Teflon (Registered Trademark) tube (an inner diameter of 0.5 mm and an outer diameter of 1/16 inch) 33 was connected, and this tube was connected to the inlet of the flow reactor 23. In addition, to the outlet of the flow reactor 23 (the Teflon (Registered Trademark) tube having inner diameter and outer diameter adjusted by residence time set), the Teflon (Registered Trademark) tube (an inner diameter of 0.5 mm and an outer diameter of 1/16 inch) 24 was connected. It should be noted that the flow reactor 23 was connected to the backpressure valve 26 via the Teflon (Registered Trademark) tube 24.

The Teflon (Registered Trademark) tubes (17, 18 and 19), which are the introduction tubes of mixed liquid of raw materials and hydrogen chloride, the mixers 20 and 21, and the flow reactor 23 were immersed in a water tank (not shown), whose temperature was adjusted as shown in Table 1. In addition, temperature of the connection part of the flow passage 24 and the backpressure valve 26 was adjusted at 15° C. by the cold insulation unit 25. The discharge line 27 from the backpressure valve 26 was installed with the discharge gas line 63, and connected to a flask as the water-containing reaction liquid trapping unit 28.

Using the above apparatus, methanol dehydrated on the molecular sieve 3A 1/8 (produced by Wako Pure Chemical Co. Ltd.) was fed in a flow rate of 12.37 mmol/min using the liquid feeding pump 10, and acetonitrile dehydrated on the molecular sieve 3A 1/8 (produced by Wako Pure Chemical Co. Ltd.) was fed in a flow rate of 24.29 mmol/min using the liquid feeding pump 11. In addition, hydrogen chloride gas was depressurized to 0.4 MPa (confirmed by the pressure gage 16) using the depressurizer 13, and then flow amount thereof was adjusted at 0.8 to 1.0 g/min using the precise needle valve 15 while confirming the flow rate by the area type flow meter 14. Acetonitrile, methanol and hydrogen chloride were supplied for 300 seconds by adjustment of flow amount of the liquid feed pump and flow amount of hydrogen chloride gas, so that reaction liquid composition is acetonitrile:methanol:hydrogen chloride=1.0:0.5:1.1, in molar ratio, and subjected to a reaction by adjustment and control of flow amount of acetonitrile, methanol and hydrogen chloride, along with the inner diameter and length of the reaction unit of the flow reactor, so that average residence time in the flow reactor 23 is such time as shown in Table 1, to yield a solution containing methyl acetimidate.

Reaction liquid quenched by the water-containing reaction liquid trapping unit 28 was stirred for 10 minutes at 25° C. to be completely hydrolyzed. Then, pH was adjusted at 3 to 9, by using an aqueous solution of 20% by mass of sodium hydroxide, and conversion rate of acetonitrile was analyzed by gas chromatography by using tetrahydrofran as an internal standard. The conversion rate based on methanol is shown in Table 1.

Examples 12 to 20

Acetonitrile, methanol and hydrogen chloride were supplied for 300 seconds by adjustment of a liquid feed pump and flow amount of hydrogen chloride gas, so that reaction liquid composition is acetonitrile:methanol:hydrogen chloride=1.0:1.1:1.1, in molar ratio, and conversion rate of acetonitrile was analyzed in the same way as in Example 1. The conversion rate based on methanol is shown in Table 2.

Example 21

A methyl acetimidate hydrochloride was produced by using an apparatus shown in FIG. 3.

The discharge line 27 from the backpressure valve 26 of FIG. 3 was introduced into a 500-mL 4-necked glass flask (the reaction liquid trapping unit 52) equipped with a stirrer and a thermometer. Furthermore, to the above flask, the Teflon (Registered Trademark) tube (an inner diameter of 0.5 mm and an outer diameter of 1/16 inch) 30, which was connected to the liquid feeding pump (produced by Shimadzu Corp.) 12 for supplying a mixture of methanol and xylene, was connected.

Acetonitrile, methanol and hydrogen chloride were reacted at an average residence time in the flow reactor 23 of 200 seconds, and a reaction temperature of 30° C., by adjustment of flow rate of dehydrated methanol to be 12.37 mmol/min using the liquid feeding pump 10, and flow rate of dehydrated acetonitrile to be 24.29 mmol/min using the liquid feeding pump 11, and flow rate of hydrogen chloride gas to be 26.71 mmol/min using a precise needle valve, to yield a solution containing a methyl acetimidate hydrochloride. Temperature of the flask (the reaction liquid trapping unit 52) was adjusted to 30° C. using a water bath (the temperature adjustment apparatus 51). To the above solution, at the same time of trapping under stirring, a mixed solution of dehydrated methanol and xylene was supplied (in a flow rate of methanol of 14.58 mmol/min and a flow rate of xylene of 2.47 g/min) using the liquid feeding pump 12. After 1 hour, supply of raw materials was stopped, the reaction mixed liquid was subjected to a reaction at the same temperature for 300 minutes to yield slurry containing crystal of a methyl acetimidate hydrochloride. Conversion rate of acetonitrile was analyzed by gas chromatography and found to be 100% based on methanol. Yield of the methyl acetimidate hydrochloride was determined by gas chromatography after derivatization to ortho-methyl acetate by the following method, because methyl acetimidate hydrochloride is an unstable compound.

The above slurry containing crystal of the methyl acetimidate hydrochloride was neutralized by the addition of 18.9% by mass of ammonia/methanol, to adjust a pH at 4.0, and then it was subjected to a reaction at 40° C. for 3 hours, under stirring. After completion of the reaction, by-produced ammonium chloride was filtered using a pressurized filter, and then yield of ortho-methyl acetate contained in the filtrate was analyzed using ortho-dichlorobenzene as internal standard. As a result, yield of the methyl acetimidate hydrochloride was found to be 93%.

Furthermore, generation amounts of acetamide, as a decomposed by-product amide compound of the methyl acetimidate hydrochloride, methyl chloride as an alkyl halide, and trimethyltriazine as triazine compound, which is a cyclic by-product compound of acetonitrile, contained in the filtrate, were analyzed by gas chromatography and found acetamide to be 1.46%, methyl chloride to be 1.46% and trimethyltriazine to be 0.18%, based on acetonitrile.

Example 22

A methyl acetimidate hydrochloride was produced by using an apparatus shown in FIG. 4.

A 200-mL 4-necked glass flask (the reaction liquid trapping unit 52) was immersed in a water bath (the temperature adjustment apparatus 51) adjusted at a temperature of 10° C., and the tigon tube (an inner diameter of 1.0 mm, and an outer diameter of 3.0 mm) 53 was inserted into the 4-necked flask. The tigon tube 53 is connected to the Teflon (Registered Trademark) tube (an inner diameter of 1.0 mm and an outer diameter of 1/16 inch) 58 by the connection tube 55 via the tube pump 54. To the inlet of the mixer (a 3-way union, produced by Swagelok Co., Ltd.) 59 of the flow reaction device, the Teflon (Registered Trademark) tube 58 for introducing reaction liquid, and the Teflon (Registered Trademark) tube (an inner diameter of 1.0 mm and an outer diameter of 1/16 inch) 57, which was connected to the liquid feed pump (produced by Shimadzu Corp.) 56 for supplying methanol, were connected, and to the outlet, the Teflon (Registered Trademark) tube (an inner diameter of 1.0 mm and an outer diameter of 1/16 inch) 62 was connected. Then, the tube was connected to the inlet of the flow reactor 64, and a Teflon (Registered Trademark) tube (an inner diameter of 1.0 mm and an outer diameter of 1/16 inch) was connected to the outlet.

The mixer 59 of the flow reaction device, the Teflon (Registered Trademark) tubes (57 and 58), the flow reactor 64 and the outflow part 60 were immersed in a water tank having temperature adjusted at 10° C.

The outflow part 60 from the flow reactor 64 is connected to the reaction liquid trapping unit 61, which contains an aqueous solution (AK) of 20% sodium hydroxide, and the reaction liquid trapping unit 61 is provided with the discharge gas line 63.

Using this apparatus, 150 g of reaction liquid of separately synthesized acetimide ether ($AI_1$, a conversion rate of 35%, composition: 18.6% my mole of acetimide ether hydrochloride, 34.6% by mole of acetonitrile, 7.0% by mole of methanol and 39.8% by mole of hydrogen chloride) was charged into the 4-necked flask 52. In addition, methanol sufficiently dried by molecular sieve 3A was charged to an HPLC pump supplying unit (not shown).

Flow rate of the pump 54 was adjusted so that flow rate inside the Teflon (Registered Trademark) tube 58 was 0.55 mL/s, and at the same time, the HPLC pump 56 was set so that flow rate inside the tube 57 was 0.11 mL/s (flow rate inside the reaction unit of the flow reactor was 0.66 mL/s, and residence time was 71 s).

Conversion rate of acetonitrile was determined by analysis of a solution trapped by the reaction liquid trapping unit 61, by gas chromatography. As a result, conversion rate of acetonitrile in the reaction liquid of acetimide ether was found to be 45%.

TABLE 1

| Example | Temperature (° C.) | Residence time (s) | Conversion rate of acetonitrile (%) |
|---|---|---|---|
| 1 | 10 | 80 | 16 |
| 2 | 10 | 200 | 36 |
| 3 | 10 | 480 | 78 |
| 4 | 20 | 80 | 28 |
| 5 | 20 | 200 | 80 |
| 6 | 20 | 480 | 98 |
| 7 | 30 | 80 | 64 |
| 8 | 30 | 200 | 96 |
| 9 | 30 | 480 | 96 |
| 10 | 40 | 200 | 72 |
| 11 | 40 | 480 | 88 |

TABLE 2

| Example | Temperature (° C.) | Residence time (s) | Conversion rate of acetonitrile (%) |
|---|---|---|---|
| 12 | 10 | 80 | 0 |
| 13 | 10 | 200 | 9 |
| 14 | 10 | 480 | 16 |
| 15 | 20 | 80 | 9 |
| 16 | 20 | 200 | 20 |
| 17 | 20 | 480 | 38 |
| 18 | 30 | 80 | 18 |
| 19 | 30 | 200 | 45 |
| 20 | 30 | 480 | 56 |

Comparative Example 1

After sufficiently purging inside of the 200-mL 4-necked flask equipped with a thermometer, a reflux condenser, an introduction tube of hydrogen chloride gas and a stirrer, with nitrogen gas, 36.8 g (0.896 moles) of acetonitrile, and 14.4 g (0.449 moles) of methanol were charged into a reactor and cooled to 10° C. While maintaining temperature inside of the reactor mentioned above at 8 to 12° C., hydrogen chloride gas was blown for 30 minutes at a rate of 0.60 g/m from the introduction tube of hydrogen chloride gas. Blown amount of hydrogen chloride gas was 18.0 g (0.494 moles). As a result of analysis by gas chromatography, conversion rate of acetonitrile was found to be 10.0% based on methanol.

Comparative Example 2

After sufficiently purging inside of the 300-mL 4-necked flask equipped with a thermometer, a reflux condenser, an introduction tube of hydrogen chloride gas and a stirrer, with nitrogen gas, 36.8 g (0.896 moles) of acetonitrile, 28.8 g (0.899 moles) of methanol and 92.5 g (0.871 moles) of xylene were charged into a reactor and cooled to 10° C. While maintaining temperature inside of the reactor at 8 to 12° C., hydrogen chloride gas was blown for 30 minutes at a rate of 0.60 g/m from the introduction tube of hydrogen chloride gas. Blown amount of hydrogen chloride gas was 18.4 g (0.499 moles). As a result of analysis by gas chromatography, conversion rate of acetonitrile was found to be 5.0% based on methanol.

Comparative Example 3

After sufficiently purging inside of the 500-mL 4-necked flask equipped with a thermometer, a reflux condenser, a dropping funnel and a stirrer, with nitrogen gas, 36.8 g (0.896 moles) of acetonitrile, and 14.4 g (0.449 moles) of methanol were charged into a reactor and cooled to 10° C. under stirring. While maintaining temperature inside of the reactor at 8 to 12° C., 36.0 g (0.986 moles) of hydrogen chloride was blown for 10 hours, to be subjected to a reaction at the same temperature for 12 hours. Temperature of the reactor was adjusted at 20° C. While maintaining temperature of the reaction liquid at 18 to 22° C., 92.5 g of xylene was dropped from a dropping funnel, and then after 17.2 g (0.537 moles) of methanol was dropped, reaction liquid was subjected to a reaction at the same temperature for 12 hours to yield slurry containing crystal of a methyl acetimidate hydrochloride. Conversion rate of acetonitrile was analyzed in the same way as in Example 1 and found to be 100%. Yield of the methyl acetimidate hydrochloride was determined by gas chromatography after derivatization to ortho-methyl acetate by the following method, because the methyl acetimidate hydrochloride is an unstable compound.

The above slurry containing crystal of the methyl acetimidate hydrochloride was neutralized by the addition of an 18.9% by mass of ammonia/methanol solution, to adjust a pH at 4.0, and then it was subjected to a reaction at 40° C. for 4 hours, under stirring. After completion of the reaction, by-produced ammonium chloride was filtered under pressure. Yield of ortho-methyl acetate contained in the filtrate was analyzed using ortho-dichlorobenzene as internal standard. As a result, yield of the methyl acetimidate hydrochloride was found to be 89.8%. Furthermore, generation amounts of acetamide, as a decomposed by-product compound of the methyl acetimidate hydrochloride, methyl chloride as an alkyl halide, and trimethyltriazine as triazine compound, which is a cyclic by-product compound of acetonitrile, contained in the filtrate, were analyzed by gas chromatography and found acetamide to be 3.74%, methyl chloride to be 3.74% and trimethyltriazine to be 1.84%, based on acetnitrile.

Example 23

A methyl acetimidate hydrochloride was produced by using an apparatus shown in FIG. 2.

To the outlet of the first flow reactor 29 (the Teflon (Registered Trademark) tube with an inner diameter of 1.59 mm and an outer diameter of ⅛ inch), the Teflon (Registered Trademark) tube (an inner diameter of 0.5 mm and an outer diameter of 1/16 inch) 34 was connected, and this tube was connected to the inlet of the mixing unit of the mixer 31 (a 3-way union, produced by Swagelok Co., Ltd.). To the outlet of the mixing unit of the mixer 31, the Teflon (Registered Trademark) tube (an inner diameter of 0.5 mm and an outer diameter of 1/16 inch) 35 was connected, and this tube was connected to the inlet of the second flow reactor 32 (the Teflon (Registered Trademark) tube with an inner diameter of 2.40 mm and an outer diameter of ⅛ inch).

Flow rate of mixed liquid of dehydrated methanol and dehydrated acetonitrile (a flow rate of methanol of 12.15 mmol/min, and a flow rate of acetonitrile of 24.29 mmol/min) was adjusted using the liquid feed pump 11, and flow rate of hydrogen chloride gas was adjusted using to be 26.72 mmol/min using a precise needle valve, and methanol, acetonitrile and hydrogen chloride were subjected to a reaction at an average residence time of 200 seconds in the first flow reaction device 29, and at a reaction temperature of 30° C., to yield a solution containing a methyl acetimidate hydrochloride.

Flow rate of dehydrated methanol was adjusted at 6.07 mmol/min using the liquid feed pump 12, and the dehydrated methanol was mixed into reaction liquid discharged from the first flow reaction device 29, via the mixing unit of the mixer 31, and subjected to a reaction in the second flow reaction device 32. In the second flow reactor, the reaction was carried out under an average residence time of 400 seconds and at a reaction temperature of 30° C. Conversion rate of acetonitrile of discharged liquid from the second flow reaction device 32 was analyzed in the same way as in Example 1, and conversion rate of acetonitrile was found to be 70% based on methanol.

Temperature of the flask (not shown) charged with 132 g of xylene was adjusted at 30° C. using a water bath (not shown). At the same time of trapping under stirring the discharged liquid from the second flow reaction device, mixed liquid of dehydrated methanol and xylene (a flow rate of methanol of 8.67 mmol/min, and a flow rate of xylene of 0.28 g/min) was supplied, using a liquid feed pump (not shown). After 60 minutes, supply of raw materials was stopped, and the reaction mixed liquid was subjected to a reaction at the same temperature for 300 minutes to yield slurry, which contains crystal of a methyl acetimidate hydrochloride. Conversion rate of acetonitrile was analyzed by gas chromatography, however, acetonitrile was not detected in the slurry.

The resultant reaction liquid was derivatized to ortho-methyl acetate in the same way as in Example 21, and as a result, yield thereof was found to be 94%.

Example 24

A methyl acetimidate hydrochloride was produced by using an equivalent apparatus shown in FIG. 3.

A mixer and a flow reaction device were connected using a Teflon (Registered Trademark) tube (an inner diameter of 4.35 mm and an outer diameter of ¼ inch), and as the flow reactor 23, a spiral reaction apparatus (produced by Kurose Chemical Equipment Co., Ltd.: a volume of the heat transfer unit of 0.61 L, and a heat transfer area of 0.3 m$^2$) was used, and as the reaction liquid trapping unit 52, a reaction vessel (with glass lining, and a volume of 200 L,) was used.

Flow rate of dehydrated methanol was adjusted to be 784 mmol/min using the liquid feed pump 10, flow rate of dehydrated acetonitrile was adjusted to be 1567 mmol/min using the liquid feed pump 11, and flow rate of hydrogen chloride gas was adjusted to be 1724 mmol/min using a precise needle valve, and a reaction was carried out at an average residence time of 200 seconds, at an introduction temperature of reaction liquid of 75 to 80° C. and at an exit temperature of reaction liquid of 30° C., to yield a solution containing a methyl acetimidate hydrochloride. Temperature of xylene (38.8 kg) charged into a reaction vessel, as the reaction liquid trapping unit 52, was adjusted at 20° C., by flowing a refrigerant medium through a jacket. At the same time of trapping under stirring the discharged liquid from the second flow reaction device, mixed liquid of dehydrated methanol and xylene (a flow rate of methanol of 940 mmol/min, and a flow rate of xylene of 30.1 g/min) was supplied using the liquid feed pump 12. By supplying raw materials for 5 hours to the reaction vessel, as the reaction liquid trapping unit 52, which was adjusted at 20° C., the reaction mixed liquid was subjected to a reaction at the same temperature for 300 minutes to yield slurry containing crystal of a methyl acetimidate hydrochloride. Conversion rate of acetonitrile was analyzed by gas chromatography, however, acetonitrile was not detected in the slurry.

The resultant reaction liquid was derivatized to ortho-methyl acetate in the same way as in Example 21, and as a result, yield thereof was found to be 90%.

Example 25

A methyl acetimidate hydrochloride was produced with temperature of a reaction vessel adjusted at 30° C., in the same way as in Example 24.

The reaction mixed liquid was subjected to a reaction at the same temperature for 300 minutes to yield slurry, which contains crystal of a methyl acetimidate hydrochloride. Conversion rate of acetonitrile was analyzed by gas chromatography, however, acetonitrile was not detected in the slurry.

The resultant reaction liquid was derivatized to ortho-methyl acetate in the same way as in Example 21, and as a result, yield thereof was found to be 89%.

Example 26

A methyl acetimidate hydrochloride was produced by using an equivalent apparatus shown in FIG. 2.

A mixer and a flow reaction device were connected using a Teflon (Registered Trademark) tube (an inner diameter of 4.35 mm and an outer diameter of ¼ inch), and as the flow reactor 29, a core and shell reactor (a volume of the heat transfer unit of 0.30 L, and a heat transfer area of 0.15 $m^2$), as the second flow reactor 32, a spiral reactor (produced by Kurose Chemical Equipment Co., Ltd.: a volume of the heat transfer unit of 0.61 L, and a heat transfer area of 0.3 $m^2$), and as the reaction liquid trapping unit 28, a reaction vessel (with glass lining, and a volume of 200 L,) were used.

Flow rate of dehydrated methanol was adjusted to be 392 mmol/min using the liquid feed pump 10, flow rate of dehydrated acetonitrile was adjusted to be 784 mmol/min using the liquid feed pump 11, and flow rate of hydrogen chloride gas was adjusted to be 862 mmol/min using a precise needle valve, and a reaction was carried out at an average residence time in the first flow reactor of 200 seconds, at an introduction temperature of reaction liquid of 75 to 80° C. and at an exit temperature of reaction liquid of 30° C., to yield a solution containing a methyl acetimidate hydrochloride.

Flow rate of dehydrated methanol was adjusted at 196 mmol/min using the liquid feed pump 12, and the dehydrated methanol was mixed into reaction liquid discharged from the first flow reaction device 29, via the mixing unit of the mixer 31, and subjected to a reaction in the second flow reaction device 32. In the second flow reactor, the reaction was carried out under an average residence time of 400 seconds and at a reaction temperature of 30° C. Conversion rate of acetonitrile of discharged liquid from the second flow reaction device 32 was analyzed in the same way as in Example 1, and conversion rate of acetonitrile was found to be 60% based on methanol.

Temperature of the reaction vessel charged with 42.5 kg of xylene was adjusted at 20° C. by flowing a refrigerant medium through the jacket thereof. At the same time of trapping under stirring the discharged liquid from the second flow reaction device, mixed liquid of dehydrated methanol and xylene (a flow rate of methanol of 274 mmol/min, and a flow rate of xylene of 8.8 g/min) was supplied, using a liquid feed pump (not shown). After 10 hours, supply of raw materials was stopped, and the reaction mixed liquid was subjected to a reaction at the same temperature for 300 minutes to yield slurry, which contains crystal of a methyl acetimidate hydrochloride. Conversion rate of acetonitrile was analyzed by gas chromatography, however, acetonitrile was not detected in the slurry.

The resultant reaction liquid was derivatized to ortho-methyl acetate in the same way as in Example 21, and as a result, yield thereof was found to be 89%.

Example 27

A methyl acetimidate hydrochloride was produced by using an equivalent apparatus shown in FIG. 3.

A mixer and a flow reaction device were connected using a Teflon (Registered Trademark) tube (an inner diameter of 4.35 mm and an outer diameter of ¼ inch), as the flow reactor 23, a spiral reaction apparatus (produced by Kurose Chemical Equipment Co., Ltd.: a volume of the heat transfer unit of 0.61 L, and a heat transfer area of 0.3 $m^2$), and as the reaction liquid trapping unit 52, a reaction vessel (with glass lining, and a volume of 200 L,) were used.

Flow rate of dehydrated methanol was adjusted to be 392 mmol/min using the liquid feed pump 10, flow rate of dehydrated acetonitrile was adjusted to be 784 mmol/min using the liquid feed pump 11, and flow rate of hydrogen chloride gas was adjusted to be 862 mmol/min using a precise needle valve, and a reaction was carried out at an average residence time in the flow reactor of 200 seconds, at an introduction temperature of reaction liquid of 75 to 80° C. and at an exit temperature of reaction liquid of 30° C., to yield a solution containing a methyl acetimidate hydrochloride. Temperature of xylene (38.8 kg) charged into the reaction vessel, which is the reaction liquid trapping unit 52, was adjusted at 20° C. by flowing a refrigerant medium through the jacket thereof. At the same time of trapping the liquid mentioned above under stirring, mixed liquid of dehydrated methanol and xylene (a flow rate of methanol of 940 mmol/min, and a flow rate of xylene of 30.1 g/min) was supplied, using the liquid feed pump 12. By supplying raw materials for 5 hours to the reaction vessel, which is the reaction liquid trapping unit 52 whose temperature being adjusted at 20° C., the reaction mixed liquid was subjected to a reaction at the same temperature for 300 minutes to yield slurry containing crystal of a methyl acetimidate hydrochloride. Conversion rate of acetonitrile was analyzed by gas chromatography, however, acetonitrile was not detected in the slurry. The resultant reaction liquid was derivatized to ortho-methyl acetate in the same way as in Example 21, and as a result, yield thereof was found to be 90%.

Example 28

An ethyl acetimidate hydrochloride was produced, in the same way as in Examples 1 to 11.

Acetonitrile, ethanol and hydrogen chloride were subjected to a reaction at 30° C., and at average residence time in the reaction unit of the flow reactor to be 200 seconds, by adjustment of flow amount of the liquid feed pump and flow amount of hydrogen chloride gas, so that reaction liquid composition is acetonitrile:ethanol:hydrogen chloride=1.0:0.5:1.1, in molar ratio, to yield a solution containing ethyl acetimidate. As a result of analysis in the same way as in Examples 1 to 11, conversion rate of acetonitrile was found to be 93.2% based on ethanol.

INDUSTRIAL APPLICABILITY

The present invention is useful due to being capable of producing an imide ether compound in a short period of time, and simply and conveniently.

This application is based on Japanese patent application No. 2005-010947 filed in Japan on Jan. 18, 2005, and the disclosure thereof is incorporated by reference in its entirety.

The invention claimed is:

1. A method for producing an imide ether compound represented by the general formula (4), wherein a nitrile compound represented by the general formula (1), an alcohol represented by the general formula (2), and a hydrogen halide represented by the general formula (3) are continuously introduced into a flow reaction device comprising a mixer and a flow reactor, to be subjected to a reaction:

(Formula 1)

$R^1CN$           (1)

(wherein $R^1$ represents a hydrogen atom, or a C1 to C12 hydrocarbon group or aryl group, which may have a substitution group, or may contain an atom other than carbon, in the structure), (Formula 2)

$$R^2OH \qquad (2)$$

(wherein $R^2$ represents a C1 to C12 hydrocarbon group), (Formula 3)

$$HX \qquad (3)$$

(wherein X represents a chlorine atom, a bromine atom or an iodine atom), (Formula 4)

$$R^1C(OR^2)=NH\cdot HX \qquad (4)$$

(wherein $R^1$ represents a hydrogen atom, or a C1 to C12 hydrocarbon group or aryl group, which may have a substitution group, or may contain an atom other than carbon, in the structure; $R^2$ represents a C1 to C12 hydrocarbon group; and X represents a chlorine atom, a bromine atom or an iodine atom).

2. The method for producing an imide ether compound according to claim 1, wherein introducing ratio into said flow reactor is 0.5 to 3.0 moles of said alcohol and 0.5 to 3.0 moles of said hydrogen halide, relative to 1 mole of said nitrile compound.

3. The method for producing an imide ether compound according to claim 1 wherein after mixing said nitrile compound and said alcohol in said mixer, said mixed liquid and said hydrogen halide are continuously introduced into said flow reactor, to be subjected to a reaction.

4. The method for producing an imide ether compound according to claim 1 wherein after mixing said alcohol and said hydrogen halide in said mixer, said mixed liquid and said nitrile compound are continuously introduced into said flow reactor, to be subjected to a reaction.

5. The method for producing an imide ether compound according to claim 1, wherein said flow reaction device, said mixer has a mixing unit with an equivalent diameter of 10 to 300,000 µm, and said flow reactor has a reaction unit with an equivalent diameter of 50 to 300,000 µm.

6. A method for producing an imide ether compound represented by the general formula (4), wherein a nitrile compound represented by the general formula (1), an alcohol represented by the general formula (2) in a ratio of 0.3 to 0.7 mole, and a hydrogen halide represented by the general formula (3) in a ratio of 0.8 to 3.0 moles, relative to 1 mole of said nitrile compound, are continuously introduced into a first flow reaction device comprising a mixer and a flow reactor, and then a reaction solution containing the resultant imide ether compound, and said alcohol in a ratio that total amount of said alcohol is 1.0 to 3.0 moles, relative to 1 mole of said nitrile compound, are continuously introduced into a second flow reaction device, to be subjected to a reaction:

(Formula 1)

$$R^1CN \qquad (1)$$

(wherein $R^1$ represents a hydrogen atom, or a C1 to C12 hydrocarbon group or aryl group, which may have a substitution group, or may contain an atom other than carbon in the structure, (Formula 2)

$$R^2OH \qquad (2)$$

(wherein $R^2$ represents a C1 to C12 hydrocarbon group), (Formula 3)

$$HX \qquad (3)$$

(wherein X represents a chlorine atom, a bromine atom or an iodine atom), (Formula 4)

$$R^1C(OR^2)=NH\cdot HX \qquad (4)$$

(wherein $R^1$ represents a hydrogen atom, or a C1 to C12 hydrocarbon group or aryl group, which may have a substitution group, or may contain an atom other than carbon in the structure; $R^2$ represents a C1 to C12 hydrocarbon group; and X represents a chlorine atom, a bromine atom or an iodine atom).

7. The method for producing an imide ether compound according to claim 6, wherein said first flow reaction device, said mixer has a mixing unit with an equivalent diameter of 10 to 300,000 µm, said first flow reactor has a reaction unit with an equivalent diameter of 10 to 300,000 µm, and said second flow reactor has a reaction unit with an equivalent diameter of 50 to 300,000 µm.

8. A method for producing an imide ether compound represented by the general formula (4), wherein a nitrile compound represented by the general formula (1), an alcohol represented by the general formula (2) in a ratio of 0.3 to 0.7 mole, and a hydrogen halide represented by the general formula (3) in a ratio of 0.8 to 3.0 moles, relative to 1 mole of said nitrile compound, are continuously introduced into a flow reaction device comprising a mixer and a flow reactor, and then a reaction solution containing the resultant imide ether compound, and said alcohol in a ratio that total amount of said alcohol is 1.0 to 3.0 moles, relative to 1 mole of said nitrile compound, are continuously subjected to a reaction:

(Formula 1)

$$R^1CN \qquad (1)$$

(wherein $R^1$ represents a hydrogen atom, or a C1 to C12 hydrocarbon group or aryl group, which may have a substitution group, or may contain an atom other than carbon in the structure), (Formula 2)

$$R^2OH \qquad (2)$$

(wherein $R^2$ represents a C1 to C12 hydrocarbon group), (Formula 3)

$$HX \qquad (3)$$

(wherein X represents a chlorine atom, a bromine atom or an iodine atom), (Formula 4)

$$R^1C(OR^2)=NH\cdot HX \qquad (4)$$

(wherein $R^1$ represents a hydrogen atom, or a C1 to C12 hydrocarbon group or aryl group, which may have a substitution group, or may contain an atom other than carbon in the structure; $R^2$ represents a C1 to C12 hydrocarbon group; and X represents a chlorine atom, a bromine atom or an iodine atom).

9. The method for producing an imide ether compound according to claim 8, wherein said flow reaction device, said mixer has a mixing unit with an equivalent diameter of 10 to 300,000 μm, and said flow reactor has a reaction unit with an equivalent diameter of 10 to 300,000 μm.

10. A method for producing an imide ether compound represented by the general formula (4), wherein a nitrile compound represented by the general formula (1), an alcohol represented by the general formula (2) in a ratio of 0.3 to 0.7 mole, and a hydrogen halide represented by the general formula (3) in a ratio of 0.8 to 3.0 moles, relative to 1 mole of said nitrile compound, are subjected to a reaction to yield a reaction solution containing an imide ether compound, and then said reaction solution, and said alcohol in a ratio that total amount of said alcohol is 1.0 to 3.0 moles, relative to 1 mole of said nitrile compound, are continuously introduced into a flow reaction device comprising a mixer and a flow reactor, to be subjected to a reaction:

(Formula 1)

$$R^1CN \quad (1)$$

(wherein $R^1$ represents a hydrogen atom, or a C1 to C12 hydrocarbon group or aryl group, which may have a substitution group, or may contain an atom other than carbon in the structure), (Formula 2)

$$R^2OH \quad (2)$$

(wherein $R^2$ represents a C1 to C12 hydrocarbon group), (Formula 3)

$$HX \quad (3)$$

(wherein X represents a chlorine atom, a bromine atom or an iodine atom), (Formula 4)

$$R^1C(OR^2)=NH \cdot HX \quad (4)$$

(wherein $R^1$ represents a hydrogen atom, or a C1 to C12 hydrocarbon group or aryl group, which may have a substitution group, or may contain an atom other than carbon in the structure; $R^2$ represents a C1 to C12 hydrocarbon group; and X represents a chlorine atom, a bromine atom or an iodine atom).

11. The method for producing an imide ether compound according to claim 10, wherein said flow reaction device, said mixer has a mixing unit with an equivalent diameter of 50 to 300,000 and said flow reactor has a reaction unit with an equivalent diameter of 50 to 300,000 μm.

* * * * *